United States Patent
Urchuk et al.

[11] Patent Number: 6,148,057
[45] Date of Patent: Nov. 14, 2000

[54] APPARATUS AND METHOD FOR CALIBRATING DETECTORS IN A COMPUTED TOMOGRAPHY SCANNER

[75] Inventors: Steven N. Urchuk, Melrose; Carl R. Crawford, Brookline, both of Mass.

[73] Assignee: Analogic Corporation, Peabody, Mass.

[21] Appl. No.: 09/184,808

[22] Filed: Nov. 2, 1998

[51] Int. Cl.[7] .............................. G01D 18/00; A61B 6/00
[52] U.S. Cl. .............................................. 378/18; 378/207
[58] Field of Search .................................. 378/4, 18, 207, 378/901; 250/252.1

[56] References Cited

U.S. PATENT DOCUMENTS

| | | | |
|---|---|---|---|
| 4,225,789 | 9/1980 | Albrecht | 250/445 |
| 4,352,020 | 9/1982 | Horiba et al. | 378/18 |
| 4,497,061 | 1/1985 | Houndsfield | 378/18 |
| 4,873,707 | 10/1989 | Roberson | 378/18 |
| 5,095,431 | 3/1992 | Feldman et al. | 364/413.13 |
| 5,214,578 | 5/1993 | Cornuejols et al. | 364/413.13 |
| 5,335,260 | 8/1994 | Arnold | 378/18 |
| 5,539,799 | 7/1996 | Schulze-Ganzlin et al. | 378/18 |
| 5,774,519 | 6/1998 | Lindstrom et al. | 378/18 |

*Primary Examiner*—Donald Hajec
*Assistant Examiner*—Drew A. Dunn
*Attorney, Agent, or Firm*—McDermott, Will & Emery

[57] ABSTRACT

A method and apparatus for calibrating detectors in a computed tomography (CT) system to compensate for differential errors in the detectors are disclosed. Multiple sets of scan data are acquired for a phantom at multiple thicknesses of the phantom. The phantom can be made from multiple slabs of material positioned on the scanner table in a horizontal orientation or in a vertical orientation. Horizontal slabs are removed or added to the stack of slabs to vary the thickness of the phantom. With vertically oriented slabs, each slab is of a different height such that scans of different slabs produce X-ray data for rays having different path lengths and, therefore, attenuations. For each detector, errors in the scan data at the multiple phantom thicknesses are identified and fit to a parametric equation with respect to the log attenuation associated with each thickness. In one embodiment, the parametric equation is a quadratic polynomial. The polynomial is used during subsequent scanning of actual objects to adjust attenuation measurements.

52 Claims, 5 Drawing Sheets

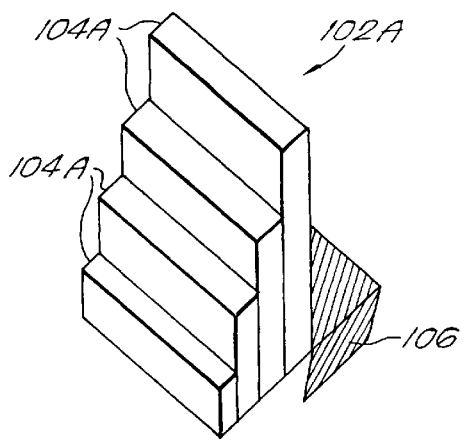 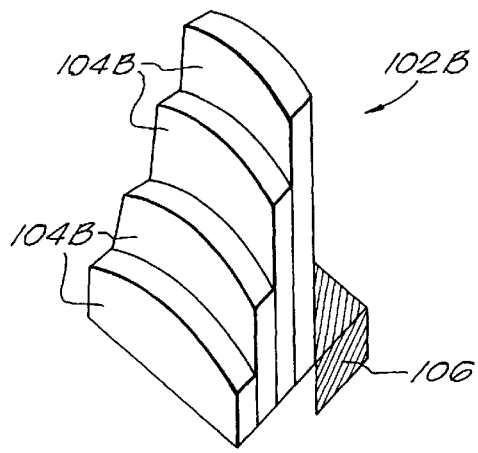
*FIG. 3A*  *FIG. 3B*
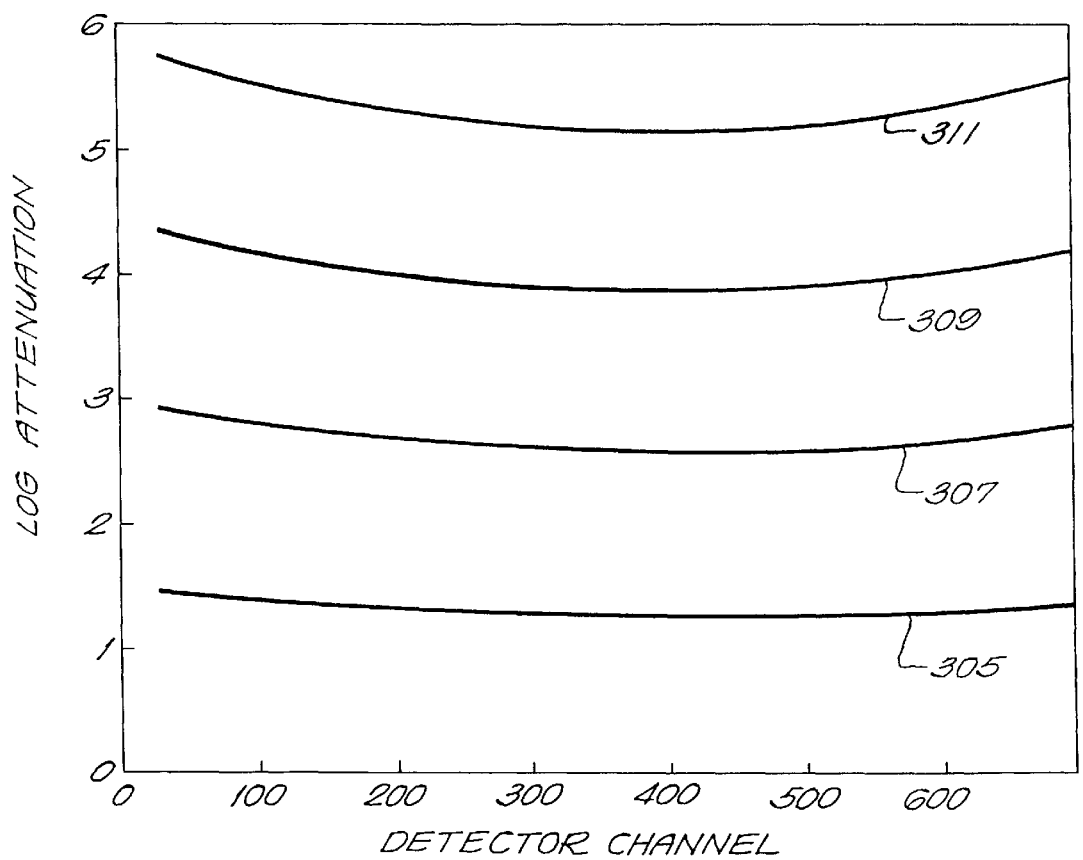
*FIG. 4*

APPARATUS AND METHOD FOR CALIBRATING DETECTORS IN A COMPUTED TOMOGRAPHY SCANNER

FIELD OF THE INVENTION

The present invention relates generally to computed tomography (CT) scanners, and more particularly to a method and apparatus for calibrating such scanners.

BACKGROUND OF THE INVENTION

CT systems of the third generation type include an X-ray source and an X-ray detector system secured to diametrically opposed sides of an annular-shaped disk. The disk is rotatably mounted within a gantry support so that during a scan, the disk continuously rotates about a rotation axis while X-rays pass from the source through an object positioned within the opening of the disk to the detector system.

The detector system typically includes an array of detectors disposed as a single row in the shape of an arc of a circle having a center of curvature at the point, referred to as the "focal spot", where the radiation emanates from the X-ray source. The X-ray source and the array of detectors are positioned so that the X-ray paths between the source and each detector all lie in the same plane (hereinafter the "slice plane" or "scanning plane") which is normal to the rotation axis of the disk. Since the X-ray paths originate from what is substantially a point source and extend at different angles to the detectors, the X-ray paths resemble a fan, and thus the term "fan beam" is frequently used to describe all of the X-ray paths at any one instant of time. The X-rays incident on a single detector at a measuring instant during a scan are commonly referred to as a "ray", and each detector generates an output signal indicative of the intensity of its corresponding ray. Since each ray is partially attenuated by all the mass in its path, the output signal generated by each detector is representative of the density of all the mass disposed between that detector and the X-ray source (i.e., the density of the mass lying in the detector's corresponding ray path).

The output signals generated by the X-ray detectors are normally processed by a signal processing portion of the CT system. The signal processing portion generally includes a data acquisition system (DAS) which filters the output signals generated by the X-ray detectors to improve their signal-to-noise ratio. The filtered output signals generated by the DAS are commonly referred to as "raw data signals." The signal processing portion usually includes a projection filter which logarithmically processes the raw data signals to generate a set of projection data signals so that each projection data signal is representative of the log attenuation produced by the mass lying in a corresponding ray path. The collection of all the projection data signals at a measuring instant is commonly referred to as a "projection" or a "view." During a single scan, as the disk rotates, a plurality of projections are generated such that each projection is generated at a different angular position of the disk. The angular orientation of the disk corresponding to a particular projection is referred to as the "projection angle."

A CT image may be generated from all the projection data signals collected at each of the projection angles. A CT image is representative of the density of a two dimensional "slice," along the scanning plane, of the object being scanned. The process of generating a CT image from the projection data signals is commonly referred to as "filtered back projection" or "reconstruction," since the CT image may be thought of as being reconstructed from the projection data. The signal processing portion normally includes a back projector for generating the reconstructed CT images from the projection data signals.

One problem with CT systems is that a variety of noise and error sources may potentially contribute noise or artifacts to the reconstructed CT images. CT systems therefore typically employ a host of signal processing techniques to improve the signal-to-noise ratio and to reduce the presence of artifacts in the reconstructed CT images.

One important factor which can cause unwanted artifacts to appear in the reconstructed CT images relates to the uniformity and stability of the X-ray detectors. If the response of a single detector is out of calibration with respect to the other detectors in the array, the single detector will cause an artifact to appear in the reconstructed CT image having the appearance of a circular ring, or one or more circular arcs, centered about the "center" of the reconstructed CT image (where the "center" of the reconstructed CT image corresponds to the location of the rotation axis of the disk). If more than one detector is out of calibration, they collectively cause a group of concentric circular rings or circular arcs to appear in the reconstructed CT image. Such artifacts are typically referred to as "rings," and "deringing" or "ring suppression" refers to methods and apparatus for reducing or eliminating the appearance of rings in the reconstructed CT images.

Ideally, the X-ray detectors are constructed so that their transfer functions or responses are all equal. However, this is difficult to achieve in practice. In many CT systems, the signal processing portion contains response calibration tables which are used to adjust the projection data signals to compensate for differences in the detector responses and thereby suppress rings in the image. The response calibration tables are typically generated by scanning objects of known density and shape, often referred to as "phantoms." The response calibration tables are updated periodically.

An important factor which can contribute to artifacts such as rings in a CT image is a phenomenon known as beam hardening, which is the change in the mean energy of the X-ray beam as it passes through a subject. Most CT scanners employ a polychromatic spectrum of X-ray energies to image a subject. Since low-energy photons tend to be preferentially attenuated, the mean energy of an X-ray beam increases as it passes through a length of material. A consequence of this beam hardening is that the projection signals vary nonlinearly with material thickness. Near the center of an object, this spectral nonlinearity decreases the CT number of the image, resulting in an image that appears cupped. The effect also produces rings and bands in third-generation scanners since they are sensitive to small differential variations in detector gain.

Methods for correcting beam hardening artifacts can involve some form of calibration to compensate detector readings for spectral nonlinearity, post processing of measured data using deringing algorithms and/or dual-energy imaging. One method for performing the nonlinear calibration involves comparing the attenuation produced by a known length of some known water-like material to its ideal value. The water-like material is used to simulate the density of soft tissue. By building a look-up table with these measurements of the known material, subsequent attenuation measurements performed on an unknown subject can be compensated for the nonlinearity of the detector readings. Use of a single bulk calibration table corrects a set of projections on average but leaves small differential gain errors between detectors. These small differential errors can be on the order of a fraction of a percent. Without further correction, these gain errors produce ring and band artifacts in reconstructed images.

At least two CT manufacturers use cylindrical plastic or water-filled phantoms to calibrate detector readings for spectral nonlinearity. In one approach, described in, for example, U.S. Pat. No. 4,352,020, issued Sep. 28, 1992, entitled, "Method and Apparatus for Examining a Subject," precisely centered plastic phantoms are scanned using a rotating CT gantry. This technique allows an estimate of attenuation to be made, since multiple rotations of data can be averaged to form each projection. However, only a limited number of attenuation measurements are obtained, due to the four or five phantoms used in the calibration procedure. As a result, a complicated interpolation and extrapolation scheme is required to generate the calibration table. In addition, the precise phantom alignment required by the technique complicates the calibration procedure, making it more labor intensive and dependent on individual operator skill.

A variant of this centered phantom approach involves scanning a single cylindrical phantom positioned off-center with respect to the center of rotation of the scanner. Such an approach is described in, for example, U.S. Pat. No. 5,214,578, issued May 25, 1993, entitled, "Method and System for the Calibration of an X-ray Scanner Using an Off-Centered Circular Phantom." This approach allows each detector channel to see a wider range of attenuation values and eliminates the need for precise centering of the phantom. However, the technique requires a homogeneous phantom with a precisely known geometry. Use of a single phantom also limits the number and range of attenuation measurements acquired.

Another method, described in U.S. Pat. No. 5,774,519, issued Jun. 30, 1998, entitled "Method of an Apparatus for Calibration of CT Scanners," involves taking scans of off-centered cylindrical water phantoms. The technique reprojects images of the water phantoms to estimate the gain errors associated with a given attenuation. This provides a range of attenuation measurements, eliminates the need to precisely center the phantom and allows inexpensive calibration phantoms to be used. However, use of a water phantom limits the number and range of attenuation measurements obtained. Also, use of reprojection makes the algorithm more computationally expensive.

SUMMARY OF THE INVENTION

The present invention is directed to an apparatus and method for calibrating a CT scanner to reduce differential errors between detector channels. The detector channels are associated with an array of detectors which is adapted to receive radiation from a radiation source to generate scan data for an object through which the radiation passes. A plurality of sets of scan data for a calibration object, for example, a phantom, are acquired at a respective plurality of thicknesses of the calibration object. Errors in the scan data at the plurality of thicknesses of the calibration object are identified. The identified errors are fit to a parametric equation with respect to a value associated with each thickness. The parametric equation is used during subsequent scanning of actual objects to adjust scan data generated by the detector channels.

In one embodiment, the parametric equation is a polynomial in the value associated with each thickness. The value associated with each thickness can be log attenuation of radiation passing through the phantom at each thickness. In one particular embodiment, the polynomial is a quadratic polynomial. Fitting the identified errors to the parametric equation can be performed by applying least-squared error analysis to the errors.

For each detector channel, a quadratic polynomial is generated and stored. During subsequent testing, for a detected log attenuation, an adjustment value is retrieved from the polynomial. These adjustment values are applied to the actual detector readings to eliminate differential errors among the detectors.

The errors in the scan data can be identified by high-pass filtering the scan data such that the average or bulk errors are removed and the differential detector errors remain. The high-pass filter can be a linear high-pass filter. The high-pass filtering can include fitting another parametric equation to the errors using a sliding fit applied to a subset of the detectors. For each detector channel, a sliding fit curve can be generated for each of the plural log attenuations, which are related to the plural phantom thicknesses. For each detector, the errors fit to the quadratic polynomial described above are calculated by determining the difference between the actual detected log attenuation and the sliding fit curve at each of the phantom log attenuation values related to the thicknesses.

In one embodiment, the calibration object or phantom includes a plurality of slabs of material. The material can include a plastic such as acrylic, polyvinyl chloride (PVC) or a calcium-embedded plastic. It can also include metal or a combination of different materials.

The slabs can be oriented horizontally in a stack located on the patient table of the scanner. The phantom thickness can be varied by adding or removing slabs. Alternatively, the slabs can be oriented vertically and have different heights. The phantom thickness can then be varied by stepping the patient table to a different position for each scan such that each scan is taken through a slab of a different height. Using this approach, the calibration procedure can be automated via automatic control of the patient table. In one particular embodiment, the top surfaces of the vertical slabs are curved such that all of the rays passing through a particular slab experience the same attenuation path length.

The present invention provides advantages over prior approaches to calibration of detectors in CT systems. By fitting gain error estimates determined by high-pass filtering projections of the slab phantoms to a phenomological curve, e.g., the quadratic polynomial in log attenuation, the approach of the invention avoids limitations inherent in prior methods, which attempt to characterize gain errors in terms of a known length of phantom material or a theoretical computed attenuation of the phantom. In the present invention, it is not required to have a prior knowledge of the thickness of the phantom material or of the actual attenuation of the material. As a result, the computation performed by the invention is simplified and has improved accuracy since it is substantially insensitive to inaccuracies in slab thickness and imperfections in the slab material.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed illustrating the principles of the invention.

FIGS. 3A and 3B contain schematic perspective views of alternative embodiments of slab phantoms in accordance with the present invention.

FIG. 4 contains a schematic plot of log attenuation versus detector channel for multiple phantom thicknesses.

DETAILED DESCRIPTION OF PREFERRED EMBODIMENTS

Figure 1:
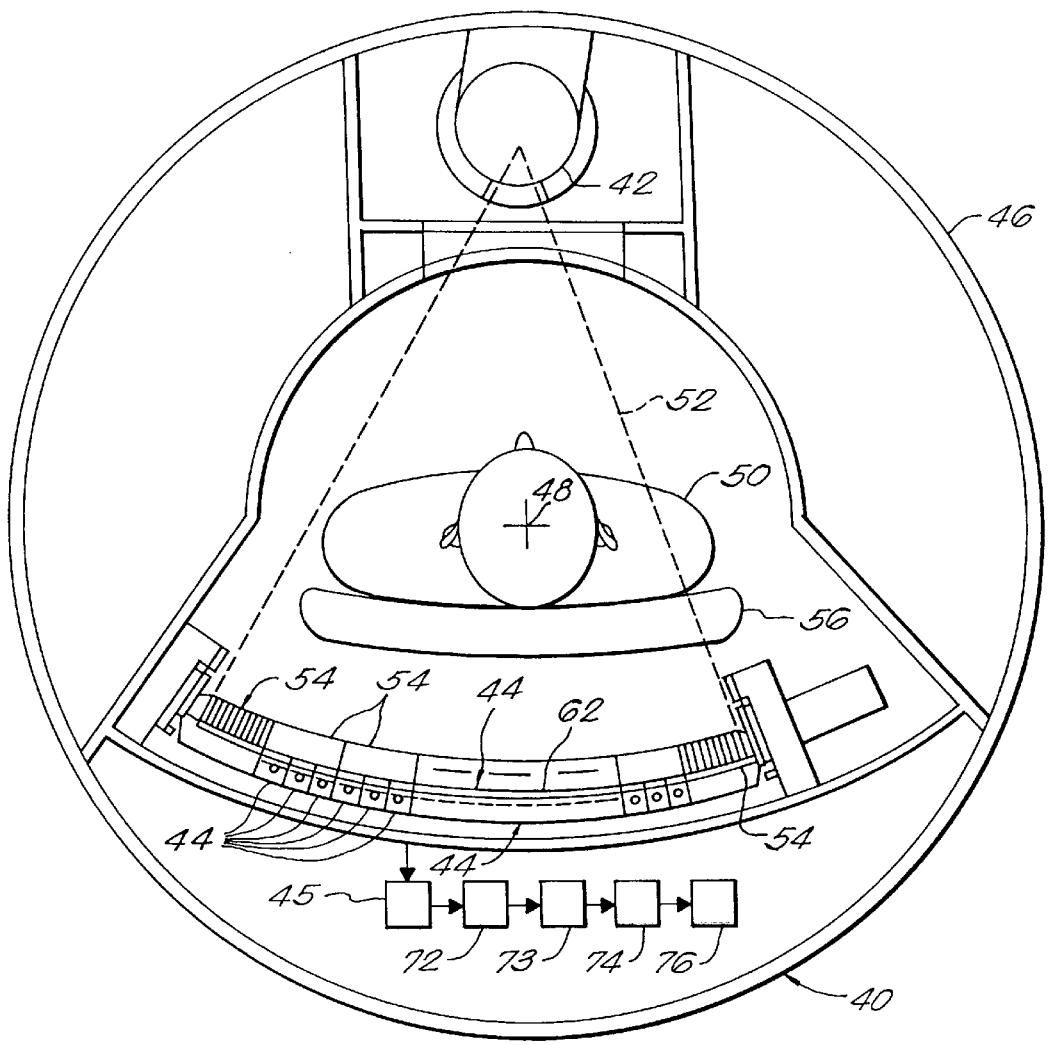
FIG. 1 is an axial view of one embodiment of a CT scanning system in accordance with the present invention.

FIG. 1 illustrates an exemplary CT system or scanner 40 incorporating the principles of the present invention. The scanner 40 includes an X-ray source 42 and a detector assembly 44 comprising an array of detectors mounted to a disk 46. Source 42 and detector assembly 44 are rotated about a rotation axis 48 extending normal to the view shown in FIG. 2 so as to rotate around the object 50 that extends through the central opening of the disk 46 during a CT scan. Object 50 may be a part of a live human patient, such as the head or torso. Source 42 emits within the scanning plane (normal to rotation axis 48) a fan-shaped beam 52 of X-rays, which are sensed by the detectors of assembly 44 after passing through object 50. An array of anti-scatter plates 54 is preferably located between object 50 and the detectors of assembly 44 to substantially prevent scattered rays from being sensed by the detectors. In a preferred embodiment the detector assembly 44 includes 384 detectors which cover an arc of 48°, although the number and angle can vary. The disk 46, which may advantageously be of a light weight material, such as aluminum, is caused to rotate rapidly and smoothly around axis 48. The disk 46 is of an open frame construction so that object 50 can be positioned through the opening of the disk. Object 50 may be supported, for example, on a table 56, which is preferably as transparent to X-rays as is practical.

During penetration of the object 50, the rays of beam 52 undergo varying degrees of attenuation. The detectors are sensitive to the incident rays and generate detector signals proportional to the amount of attenuation of radiation that passes through the object 50.

The output signals generated by the detector assembly 44 are applied to a data acquisition system (DAS) 45 (shown in block diagram form) which generates therefrom a set of raw data signals. The raw data signals are applied to a projection filter 72 which generates a set of projection data signals. As disk 46 rotates, the projection data signals are used to provide projections from many projection angles. The projection data signals can be applied to a calibration processing system 73 which can perform bulk calibration and the detector-dependent calibration of the invention. Next, the calibrated signals can be applied to a ring suppression filter 74 which filters the signals to reduce rings in the reconstructed CT images. The output signals generated by the ring suppression filter 74, referred to as "ring corrected projection data signals" or simply as "ring corrected signals," are then applied to a back projector 76 which generates the CT images from the ring corrected signals. The back projector 76 can include an input stage that includes a convolution filter for convolving the data as required for back projection.

The calibration processing system or processor 73 applies corrections to the data signals based on the calibration of the invention. The nonlinear calibration technique of the invention combines separate calibrations for both the bulk or average and the detector-dependent or differential components of spectral nonlinearity associated with beam hardening. The bulk calibration can use a polynomial-based look-up table to produce a flattened image with corrected CT numbers. Such a bulk calibration is described in, for example, "A Method for Correcting Bone Induced Artifacts in Computed Tomography Scanning," by Peter M. Joseph and Robin D. Spital, published in *Journal of Computer Assisted Tomography*, volume 2, pages 100–108 in January, 1978. Next, a detector-dependent calibration, which is the subject of the present patent application, generates a set of calibration tables that reduce the ring and band artifacts produced by the differential nonlinearity of the detectors.

To reduce the dynamic range of the calibration procedure, it is desirable to perform separate calibrations for the bulk or average portion of the detector nonlinearity and the detector-dependent or differential portions of the nonlinearity. This can be achieved because the bulk nonlinearity of a set of detector channels is typically much larger than the differential nonlinearity between channels.

For rays passing through isocenter, the gain of the central detectors should be matched to a differential on the order of 0.03% to remove rings at the center of the field of view. For detectors at larger radius, the sensitivity to differential errors decreases but remains on the order of a tenth of a percent. Large variations in the absolute accuracy of the calibration are tolerable since it is the differential error that produces ring and band artifacts.

The procedure of the invention can generate nonlinear calibration tables using a two-step process. First, a set of detector-dependent gain errors is estimated by high-pass filtering attenuation measurements performed with a stationary gantry over varying thicknesses of the calibration phantom, which, in one embodiment, is formed from multiple plastic slabs. Next, these error estimates are used to generate an array of polynomial-based look-up tables, one for each X-ray detector. The use of these tables compensates the detector readings for the differential nonlinearity of the detectors, thus reducing the amplitude of ring and band artifacts in reconstructed images.

Figure 2:
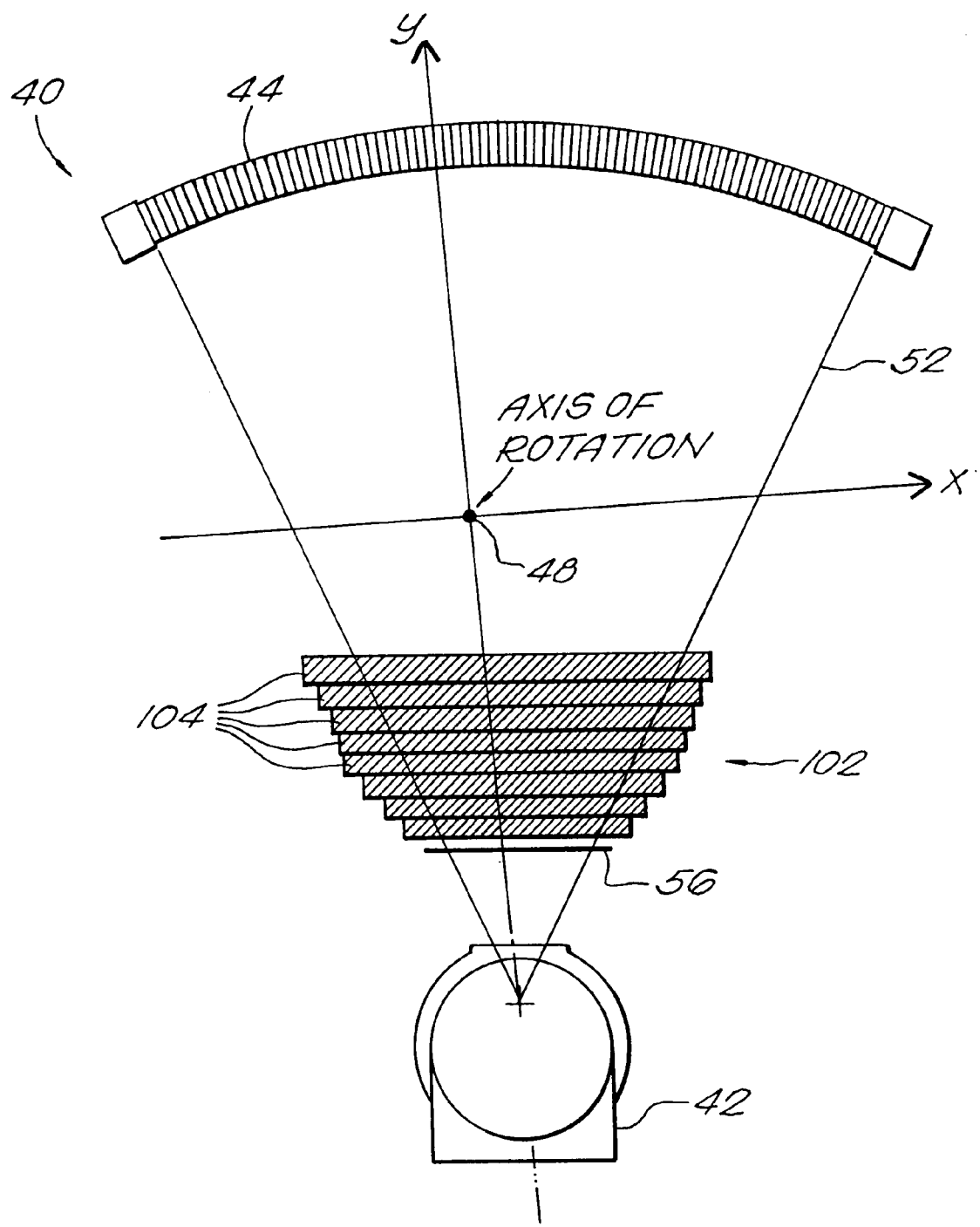
FIG. 2 is a schematic axial view of one embodiment of the CT scanning system of the invention with a slab phantom placed on the patient table to implement the calibration of the invention.

In one embodiment of the invention, a phantom which includes multiple substantially uniform plastic slabs is used to calibrate the detector system for differential gain variations. FIG. 2 is a schematic axial view of a CT system 40 in accordance with the invention in which a calibration object or phantom 102 including a plurality of horizontal stacked slabs 104 is positioned on a mounting fixture 56 positioned within the stationary CT gantry or disk 46. The attenuation presented by this phantom 102 varies slowly across the detector array 44 due to the increased path length of rays traversing the phantom at less than normal incidence. Varying degrees of attenuation across the entire array 44 can be produced by incrementally adding or removing slabs 104, thus allowing a range of attenuation values to be calibrated. In one embodiment, the slabs 104 made of a plastic material such as acrylic. This material is selected because its attenuation is close to that of soft tissue. In other embodiments, more dense materials, such as metal or human-bone-equivalent material such as polyvinyl chloride (PVC) or calcium-embedded plastics, can be used to calibrate the detectors. The slabs 104 are of sufficient width to cover the entire X-ray fan beam 52 over the full range of phantom thicknesses. FIGS. 3A and 3B are schematic perspective illustrations of alternative phantoms 102A and 102B, respectively, to the slab stack 102 of FIG. 2. In the embodiments of FIGS. 3A and 3B, the slabs 104A and 104B are mounted to the patient table 56 via a mounting bracket 106 in a vertical orientation with respect to the table 56 as shown. In these embodiments, thicknesses of the phantom used to obtain projections are varied by stepping the table 56 along the axis of rotation 48 such that, for each projection, the fan beam passes through a different slab and, as a result, experiences a different phantom thickness and path length. These types of phantoms as shown in FIGS. 3A and 3B allow for automated slab-based calibration. Manual intervention to remove and add slabs is eliminated by the automatic stepping of the patient table through the slabs. The slabs 104B shown in FIG. 3B have curved top surfaces such that, at a particular slab, all of the rays across the detector array pass through the same path length of phantom material.

FIG. 4 is a schematic plot which illustrates log attenuation versus detector channel for scans of four different thicknesses of phantom. Referring to the curves from the bottom to the top of the plot, the log attenuation curves are obtained for phantom thicknesses of two (curve 305), four (curve 307), six (curve 309) and eight (curve 311) one-inch plastic slabs, for example. As shown in the plot, the lowest level of attenuation is produced using two slabs, and the highest level of attenuation is obtained using eight slabs. The "dipped" shapes of the curves is caused by the variation in path length with detector channel in the horizontal stacked slab configuration. Because of the scale of the plot in FIG. 4, high-frequency variations produced by differential errors from detector to detector are not visible in the curves.

Figure 5:
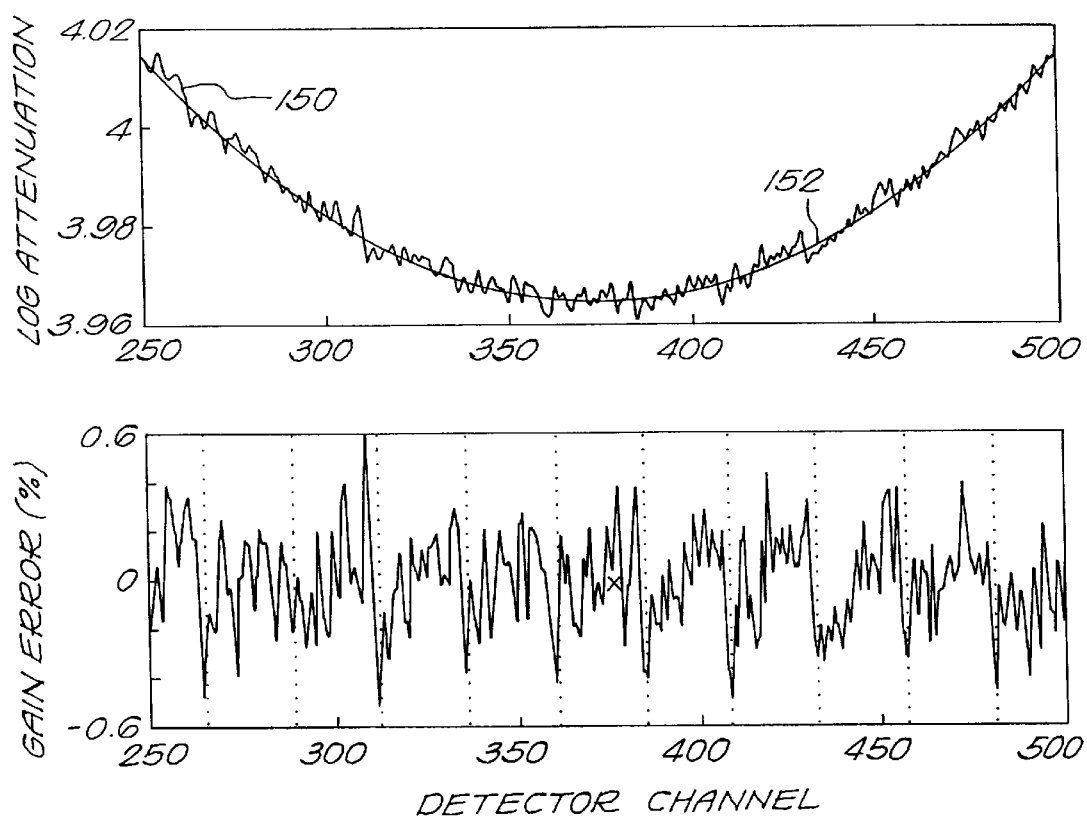
FIG. 5 contains schematic plots of log attenuation and gain error percentage versus detector channel for a single phantom thickness which illustrates the sliding curve fit approach to identifying differential detector errors in accordance with the present invention.

FIG. 5 contains schematic plots of log attenuation and gain error percentage versus detector channel for a scan at a single slab thickness. FIG. 5 is used to illustrate the procedure of the invention used to estimate gain errors for a single projection at each detector. The log attenuation plot of FIG. 5 includes two curves. One of the curves, labeled 150, is a plot of the measured projection for each individual detector. It illustrates the high-frequency or differential variation in log attenuation among the detectors. The second curve, labeled 152, is a curve that is fit to the log attenuation measurements in curve 150 by using a sliding fit in accordance with the invention. The gain error percentage plot illustrates the residuals for the errors in the log attenuation curve. That is, the gain error percentage curve shows the difference between the actual log attenuation measured at a particular detector and the value of the sliding fit curve 152 at that detector.

Figure 6:
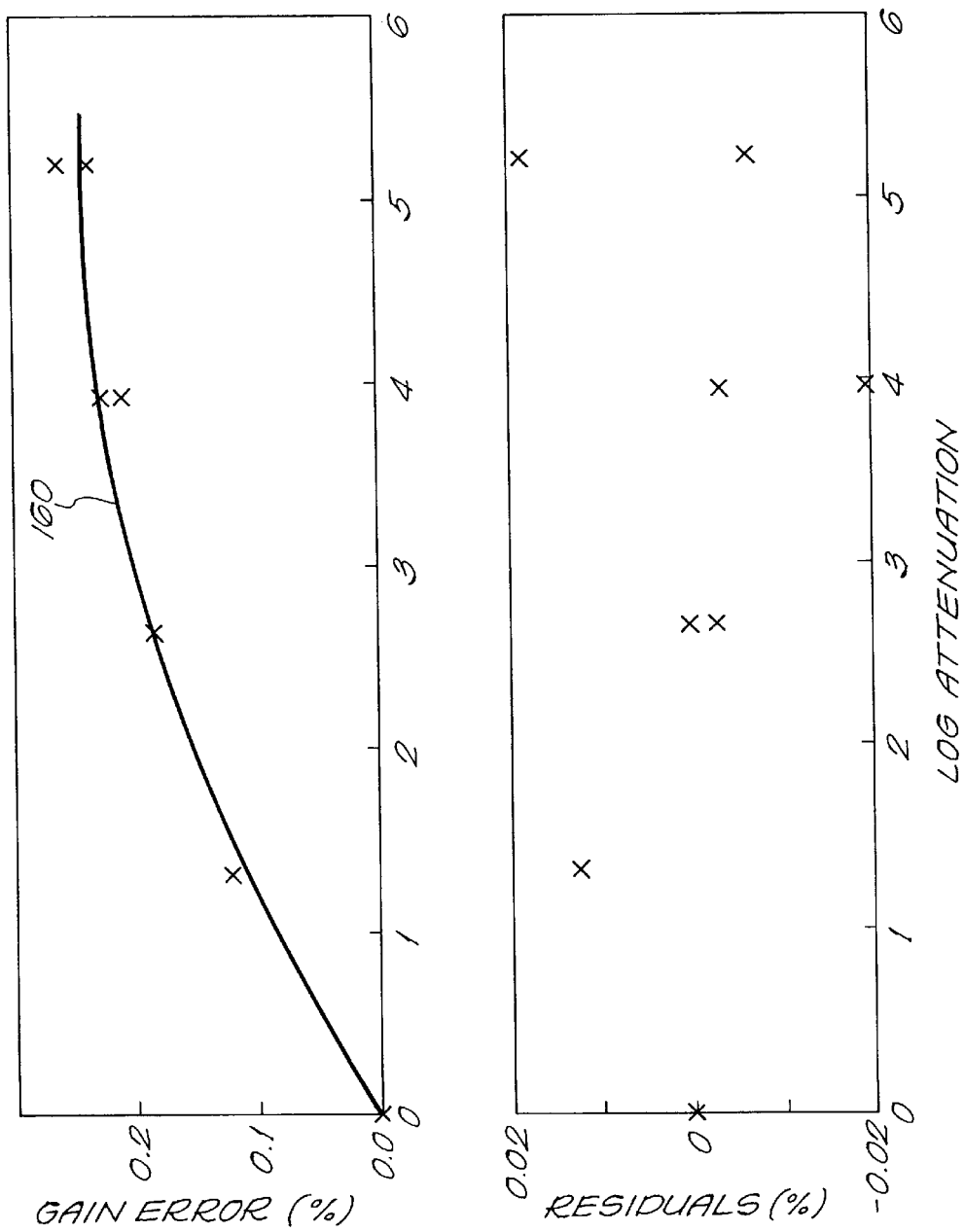
FIG. 6 contains schematic plots of gain error percentage and error residuals versus log attenuation, illustrating a quadratic polynomial fit of gain errors versus log attenuation for a single detector channel in accordance with the present invention.

In accordance with the invention, at each detector, these gain error residuals are computed for each log attenuation corresponding to each slab thickness. Therefore, for each detector, a set of gain error residuals is computed, one for each slab thickness. At each detector, these residuals are fit to a parametric equation versus log attenuation, which in one embodiment is a quadratic polynomial. FIG. 6 contains schematic plots of gain error percentage and the error residuals versus log attenuation which illustrate fitting the error residuals to the quadratic polynomial. During subsequent scans of actual subjects, each detector data value is adjusted according to the quadratic polynomial. That is, for each detector, the log attenuation value recorded is compared to the quadratic polynomial to obtain a correction factor at that attenuation. The value for the detector is adjusted accordingly.

Referring to FIG. 5, estimates of the differential gain variations are obtained from the high-frequency content of the slab projections. Since the projections of the slab phantoms are smooth and the projection data have already been compensated for their bulk nonlinearity, any high-frequency deviations in the projections can be associated with differential gain errors. The residuals of the fit of the projection data to a low-order sliding polynomial provides a good estimate of the errors. In one embodiment, a limited number of channels are used for the sliding fit to reject low-frequency variations in detector gain. In practice, in one embodiment, a quadratic polynomial equal in width to approximately one hundred detector channels is sufficient. An estimate of the gain error associated with a channel is obtained from the difference between the measurement and the fit value. This procedure is repeated over the detector array to produce an estimate of the gain error across the array produced by a given attenuation. It also produces a set of gain error estimates spanning the range of attenuation values found in head and body imaging, e.g., log attenuation values ranging from 2 to 7.

In one embodiment, the sliding fit curve 152 shown in FIG. 5 is produced by a sliding least squares fit in accordance with equation (1) below. For each detector channel d and projection j, minimize $$\chi^2[d] = \sum_{i=N_{l2}}^{N_{l2}} (y_j[i+d] - a_o[d] - a_1[d]i - a_2[d]i^2)^2 \quad (1)$$

with respect to $a_0$, $a_1$ and $a_2$. In equation (1), $y_j[d]$ is the log attenuation measured at detector d and projection j. The number of detector channels used in the fit is equal to N+1. The number of projections is M.

Next, the differential error δ or residual shown in the gain error percentage curve of FIG. 5, estimated from the fitting procedure, is given by $$\delta_j = y_j[d] - a_o[d] \quad (2).$$

The error estimates produced by the calibration procedure can include random errors due to quantam noise and systematic errors from machine instability and phantom defects. Due to these error sources, a better estimate of the gain error can be achieved by fitting the error estimates to a phenomological curve, e.g., the quadratic polynomial. This fitting is illustrated in connection with FIG. 6, which contains plots for a single detector channel at multiple slab thicknesses of gain error percentage and residual versus log attenuation. It is the gain error percentages that are fit to the phenomological curve 160 to obtain the calibration curve in accordance with the invention. From a power series expansion of the attenuation, the gain errors can be estimated as a quadratic polynomial in log attenuation. An expansion in terms of material thickness could also be used, but that would require that the phantom density and dimensions be known very accurately.

In one embodiment, the fitting of the differential errors is performed in accordance with equation (3) below. For each detector channel d, minimize $$\chi^2[d] = \sum_{j=1}^{M} (\delta_j - b_1[d]y_j[d] - b_1[d]y_j^2[d])^2 \quad (3)$$

with respect to $b_1$ and $b_2$. FIG. 6 illustrates the fitting procedure used to estimate the gain error of a single channel. The gain error plot illustrates the gain error points estimated for a given detector channel over multiple log attenuations generated at multiple phantom thicknesses. Also shown is the quadratic curve 160 fit to the data using the procedure defined by equation (3) above. Since the gain error at zero attenuation is zero, the fit is constrained to pass through the origin of the data set. The residuals from the fit are shown in the bottom plot of FIG. 6, indicating agreement between the measured data and the fit.

The parameters $b_1$ and $b_2$ are used to correct raw data for the detector-dependent beam hardening effects. Given a projection measurement $p[d]$ as input, the corrected projection $\tilde{p}[d]$ is given by $$\tilde{p}[d] = p[d] - b_1[d]p[d] - b_2[d]p[d]^2 \quad (4).$$

Each detector d has its own unique quadratic curve fit to the calibration attenuation data. During subsequent scanning, the curve is used to adjust the data for the particular detected log attenuation value. After calculation of the calibration data in accordance with the above, correction of actual input data can be achieved by building a look-up table for the input data. Several methods are possible. In one embodiment, the calibration data are converted to a 64-point look-up table. Alternative data formats of correction are possible, including use of linear and quadratic coefficients with a bulk correction.

The slab-based nonlinear calibration technique of the invention has several advantages over previous methods based on the scanning of cylindrical or rectangular phantoms. The benefits of the method of the invention arise from the novel data processing employed to generate the calibration table. Specifically, the estimation of differential gain errors from high-frequency components of the slab projections and the fitting of these gain errors to a phonological curve overcome the need to accurately know the composition and dimensions of the phantom material and/or the theoretical expected attenuation from the phantom. An advantage of not requiring a phantom to be precisely characterized is that is simplifies the calibration procedure and allows for relatively inexpensive phantoms to be constructed.

An additional advantage of using slab phantoms is that they allow calibration of all of the X-ray detectors over a uniform sampled range of attenuation values. This avoids the need for interpolation and/or extrapolation of data obtained from different phantoms, a problem associated with the use of centered cylindrical phantoms.

In one embodiment, the slab-based calibration technique of the invention collects a single attenuation measurement for each phantom thickness used. Given four increments in phantom thickness, this covers the range of expected attenuation with relatively few data points, compared to techniques used in other systems.

Ideally, one would like to estimate the gain variations produced by spectral effects alone while excluding other factors which modify the detector readings. To accomplish this, the calibration procedure of the invention can be performed relatively quickly with corrections and/or control for factors such as detector temperature variations, z-axis beam position, radiation damage and detector afterglow. The measurement geometry should minimize the sensitivity of the technique to afterglow, since the X-ray flux incident on each detector is approximately constant during data acquisition. It is also possible to minimize radiation damage effects by staging the calibration such that the radiation exposure of the detectors is minimized, e.g., the thicker sections of the phantom can be scanned first. Correction of the input data for imperfections in the X-ray window can also be performed simply due to the stationary detector geometry. Given these considerations, together with the computational efficiency of the technique, it is possible to perform the calibration procedure of the invention with a relatively short cycle time. For example, the data collection and computation required to build a single calibration table might take on the order of three minutes, excluding set-up time.

In accordance with the invention, for head imaging, a dedicated phantom may be used which includes a layer of bone-equivalent material and a layer of plastic. It may be useful to use a hybrid technique involving both slabs and a cylindrical water phantom. Near the center of the detector array, where the requirements on the calibration are most severe, gain errors could be estimated using the water phantom. Away from the water phantom, estimates from the slabs could be used. Additional calibration data might also be obtained from dual-energy scans.

While this invention has been particularly shown and described with references to preferred embodiments thereof, it will be understood by those skilled in the art that various changes in form and detail may be made therein without departing from the spirit and scope of the invention as defined by the appended claims.

What is claimed is:

1. A method of calibrating a tomographic scanner to reduce detector channel differential errors in a plurality of detector channels associated with an array of detectors, said array of detectors being adapted to receive radiation from a radiation source to generate scan data for an object through which the radiation passes, said method comprising:

acquiring a plurality of sets of scan data for a calibration object at a respective plurality of thicknesses of the calibration object;

high-pass filtering the scan data so as to identify errors in the scan data acquired for a detector channel at the respective plurality of thicknesses of the calibration object; and fitting the identified errors to a parametric equation with respect to a value associated with each thickness, said parametric equation being used during subsequent scanning of actual objects to adjust scan data generated by the detector channel.

2. The method of claim 1 wherein the parametric equation is a polynomial.

3. The method of claim 1 wherein the parametric equation is a quadratic polynomial.

4. The method of claim 1 wherein fitting the identified errors to a parametric equation comprises applying least squares error analysis to the errors.

5. The method of claim 1 wherein the high-pass filtering comprises linear high-pass filtering.

6. The method of claim 1 wherein the high-pass filtering comprises fitting a second parametric equation to the errors.

7. The method of claim 1 wherein the value associated with each thickness of the calibration object is log attenuation of radiation that passes through the calibration object.

8. The method of claim 1 wherein the calibration object comprises a plurality of slabs of material.

9. The method of claim 8 wherein the slabs are of various dimensions so that the calibration object has varying thicknesses and can be rested on a support, and the scanner and support can be moved relative to one another so as to allow a plurality of scans through corresponding thicknesses of the calibration object.

10. The method of claim 9 wherein the relative movement of the scanner and support is automated.

11. An apparatus for calibrating a tomographic scanner to reduce detector channel differential errors in a plurality of detector channels associated with an array of detectors, said array of detectors being adapted to receive radiation from a radiation source to generate scan data for an object through which the radiation passes, said apparatus comprising:

data acquisition subsystem constructed and arranged so as to acquire a plurality of sets of scan data for a calibration object at a respective plurality of thicknesses of the calibration object;

a high pass filter arrangement constructed and arranged so as to identify errors in the scan data acquired for a detector channel at the respective plurality of thicknesses of the calibration object; and an error compensation subsystem constructed and arranged so as to fit the identified errors to a parametric equation with respect to a value associated with each thickness, said parametric equation being used during subsequent scanning of actual objects to adjust scan data generated by the corresponding detector channel.

12. The apparatus of claim 11 wherein the parametric equation is a polynomial.

13. The apparatus of claim 11 wherein the parametric equation is a quadratic polynomial.

14. The apparatus of claim 11 wherein the error compensation subsystem comprises an analyzer constructed and arranged so as to apply a least squares error analysis to the errors.

15. The apparatus of claim 11 wherein the error identifier comprises a filtering arrangement constructed and arranged so as to high-pass filter the scan data.

16. The apparatus of claim 15 wherein the the filtering arrangement comprises a second error compensation subsystem constructed and arranged so as to fit a second parametric equation to the errors.

17. The apparatus of claim 11 wherein the value associated with each thickness of the calibration object is log attenuation of radiation that passes through the calibration object.

18. The apparatus of claim 11 wherein the calibration object comprises a plurality of slabs of material.

19. The apparatus of claim 18 wherein the material of the slabs comprises plastic.

20. The apparatus of claim 18 wherein the material of the slabs comprises acrylic.

21. The apparatus of claim 18 wherein the material of the slabs comprises metal.

22. The apparatus of claim 18 wherein the material of the slabs comprises calcium-embedded plastic.

23. The apparatus of claim 18 wherein the material of the slabs comprises a plurality of different materials.

24. The apparatus of claim 18 wherein the slabs are of various dimensions so that the calibration object has varying thicknesses and can be rested on a support, and the scanner and support can be moved relative to one another so as to allow a plurality of scans through corresponding thicknesses of the calibration object.

25. The apparatus of claim 24 wherein the relative movement of the scanner and support is automated.

26. A method of calibrating a tomographic scanner to reduce detector channel differential errors in a plurality of detector channels associated with an array of detectors, said array of detectors being adapted to receive radiation from a radiation source to generate scan data for an object through which the radiation passes, said method comprising:

acquiring a plurality of sets of scan data for a calibration object at a respective plurality of thicknesses of the calibration object;

identifying errors in the scan data acquired for a detector channel at the respective plurality of thicknesses of the calibration object; and fitting the identified errors to a parametric equation with respect to a value associated with each thickness by applying a least square analysis to the errors, said parametric equation being used during subsequent scanning of actual objects to adjust scan data generated by the corresponding detector channel.

27. The method of claim 26 wherein the parametric equation is a polynomial.

28. The method of claim 26 wherein the parametric equation is a quadratic polynomial.

29. The method of claim 26 wherein fitting the identified errors to a parametric equation comprises applying least squares error analysis to the errors.

30. The method of claim 26 wherein identifying errors in the scan data comprises high-pass filtering the scan data.

31. The method of claim 30 wherein the high-pass filtering comprises linear high-pass filtering.

32. The method of claim 30 wherein the high-pass filtering comprises fitting a second parametric equation to the errors.

33. The method of claim 26 wherein the value associated with each thickness of the calibration object is log attenuation of radiation that passes through the calibration object.

34. The method of claim 26 wherein the calibration object comprises a plurality of slabs of material.

35. The method of claim 34 wherein the slabs are of various dimensions so that the calibration object has varying thicknesses and can be rested on a support, and the scanner and support can be moved relative to one another so as to allow a plurality of scans through corresponding thicknesses of the calibration object.

36. The method of claim 35 wherein the relative movement of the scanner and support is automated.

37. An apparatus for calibrating a tomographic scanner to reduce detector channel differential errors in a plurality of detector channels associated with an array of detectors, said array of detectors being adapted to receive radiation from a radiation source to generate scan data for an object through which the radiation passes, said apparatus comprising:

a data acquisition subsystem constructed and arranged so as to acquire a plurality of sets of scan data for a calibration object at a respective plurality of thicknesses of the calibration object;

a high pass filter arrangement constructed and arranged so as to identify errors in the scan data acquired for a detector channel at the respective plurality of thicknesses of the calibration object; and an error compensation subsystem constructed and arranged so as to fit the identified errors to a parametric equation with respect to a value associated with each thickness by applying a least square analysis to the errors, said parametric equation being used during subsequent scanning of actual objects to adjust scan data generated by the corresponding detector channel.

38. The apparatus of claim 37 wherein the parametric equation is a polynomial.

39. The apparatus of claim 37 wherein the parametric equation is a quadratic polynomial.

40. The apparatus of claim 37 wherein the error compensation subsystem comprises an analyzer constructed and arranged so as to apply a least squares error analysis to the errors.

41. The apparatus of claim 37 wherein the error identifier comprises a filtering arrangement constructed and arranged so as to high-pass filter the scan data.

42. The apparatus of claim 41 wherein the means for high-pass filtering the scan data comprises means for linear high-pass filtering the scan data.

43. The apparatus of claim 41 wherein the filtering arrangement comprises a second error compensation subsystem constructed and arranged so as to fit a second parametric equation to the errors.

44. The apparatus of claim 37 wherein the value associated with each thickness of the calibration object is log attenuation of radiation that passes through the calibration object.

45. The apparatus of claim 37 wherein the calibration object comprises a plurality of slabs of material.

46. The apparatus of claim 45 wherein the material of the slabs comprises plastic.

47. The apparatus of claim 45 wherein the material of the slabs comprises acrylic.

48. The apparatus of claim 45 wherein the material of the slabs comprises metal.

49. The apparatus of claim 45 wherein the material of the slabs comprises calcium-embedded plastic.

50. The apparatus of claim 45 wherein the material of the slabs comprises a plurality of different materials.

51. The apparatus of claim 45 wherein the slabs are of various dimensions so that the calibration object has varying thicknesses and can be rested on a support, and the scanner and support can be moved relative to one another so as to allow a plurality of scans through corresponding thicknesses of the calibration object.

52. The apparatus of claim 51 wherein the relative movement of the scanner and support is automated.

* * * * *